United States Patent [19]

Gozzo et al.

[11] 4,228,101
[45] * Oct. 14, 1980

[54] TWO DICHLOROACETAMIDE ANTIDOTES FOR NON-SELECTIVE HERBICIDES PARTICULARLY ACTIVE IN THE PROTECTION OF MAIZE AGAINST THE POISONOUS ACTION EXERTED BY HERBICIDES ESTERS OF N,N-DISUBSTITUTED GLYCINE

[75] Inventors: Franco Gozzo, San Donato Milanese; Luigi Abbruzzese, Milan; Giorgio Siddi, San Donato Milanese, all of Italy

[73] Assignee: Montedison S.p.A., Milan, Italy

[*] Notice: The portion of the term of this patent subsequent to Mar. 25, 1997, has been disclaimed.

[21] Appl. No.: 971,713

[22] Filed: Dec. 21, 1978

[30] Foreign Application Priority Data

Dec. 23, 1977 [IT] Italy .................... 31189 A/77

[51] Int. Cl.³ .................................. C07C 103/27
[52] U.S. Cl. ......................... 260/561 HL; 71/111; 71/118
[58] Field of Search ............... 260/561 HL; 71/118

[56] References Cited

U.S. PATENT DOCUMENTS

| 3,867,444 | 2/1975 | Baker ........................... 71/118 |
| 4,021,224 | 5/1977 | Pallos et al. .................. 71/118 |
| 4,033,756 | 7/1977 | Hoffmann .................... 71/118 |

FOREIGN PATENT DOCUMENTS

| 2402983 | 8/1974 | Fed. Rep. of Germany ............. 71/118 |
| 2747814 | 5/1978 | Fed. Rep. of Germany ............. 71/118 |

Primary Examiner—Glennon H. Hollrah

[57] ABSTRACT

Compounds of formula:

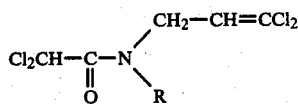

(wherein R=ethyl or 1,1-dimethylpropargyl) are useful as antidotes in protecting maize and other crops from the damages of non-selective herbicides of the N,N-disubstituted-glycine type.

3 Claims, No Drawings

TWO DICHLOROACETAMIDE ANTIDOTES FOR NON-SELECTIVE HERBICIDES PARTICULARLY ACTIVE IN THE PROTECTION OF MAIZE AGAINST THE POISONOUS ACTION EXERTED BY HERBICIDES ESTERS OF N,N-DISUBSTITUTED GLYCINE

THE PRIOR ART

Esters of N,N-disubstituted glycine exerting an herbici de activity are disclosed for example in U.S. Pat. No. 3,780,090 by Sumitomo Co. or in German Pat. Application No. 2,311,897 by Hercules Company.

The following compounds, marketed by Hercules Company proved to be very effective as disherbing agents:

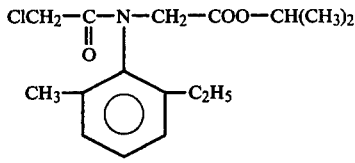

(HS 26910)

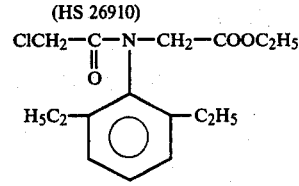

(Antor)

however they proved to be toxic even for plants of agricultural interest such as maize.

In German Patent Application DOS No. 2,402,983 by Ciba-Geigy Co. there are described antidotes for agricultural cultivations against the toxic effect of chloroacetanylide type herbicides, of formula:

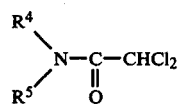

wherein $R^4$ and $R^5$ are, amongst others, alkyl, alkenyl, alkynyl optionally substituted by halogen atoms.

The compounds of formula:

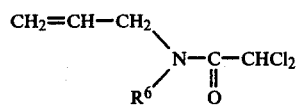

wherein $R^6$ = allyl or alkyl, are cited as particularly effective antidotes.

In U.S. Pat. No. 4,033,756 by Gulf Co. there is described the use of dichloroacetamides in coating the seeds of crops such as rice and corn in order to protect them by the injury of a variety of herbicides, particularly the thiocarbamates.

In U.S. Pat. No. 4,021,224 by Stauffer there are described herbicide compositions consisting of an herbicide (thiocarbamates or triazines) and an antidote of general formula:

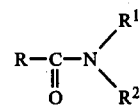

wherein R may be, amongst others, a dichloromethyl group while $R^1$ and $R^2$ represent alkyl, alkenyl and aryl groups.

In German Patent Application DOS No. 2,747,814 by the present applicants, there are described antidotes of general formula:

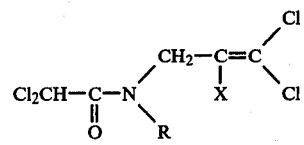

wherein
X = H, halogen
R = H, phenyl, optionally halogen-substituted alkyl alkenyl and alkynyl groups.

Said products allow the use of non-selective herbicides, such as derivatives of N,N-disubstituted glycine in disherbing of maize and wheat fields without damaging the useful plants. Particularly active in protecting maize cultivations against the damages of HS 26910 and Antor, proved to be the compound N-allyl-N-(3,3-dichloroallyl)-dichloroacetamide of formula:

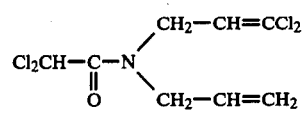

THE PRESENT INVENTION

Object of this invention are compounds of general formula:

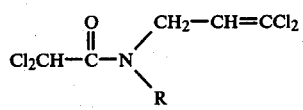

wherein R = ethyl or 1,1-dimethylpropargyl which display at least double the activity displayed by the best compounds of the Prior Art in the protection of maize against intoxications due to the herbicide compounds of general formula:

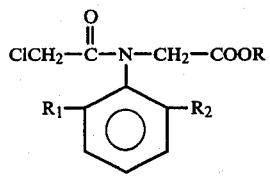

wherein R, $R^1$ and $R^2$ = alkyl.

Still another object of this invention is that of providing a method for freezing maize cultivations from infesting weeds and herbs without harming the crop itself, and which consists in treating the cultivations with a non-selective herbicide in the presence of amounts of compounds of formula I ranging from 0.05 kg/ha upward.

The non-selective herbicides and the compounds according to this invention, can be administered either separately in the form of emulsions, aqueous suspensions, powders, wettable powders etc., or, as one single composition containing from 1% to 50% by weight of antidote (or of the antidotes), of the invention with respect to the non-selective herbicides, besides the usual surfactants, fillers, diluents, etc. In order to even more clearly illustrate this invention, the following examples are given.

EXAMPLE 1

Preparation of N-(1,1-dimethylpropargyl)-N-(dichloroallyl)-dichloroacetamide (our mark: M 8991)

Into 1.2 mols of 1,1-dimethylpropargylamine there were dripped, under stirring at room temperature, 0.3 mols of 3,3,1-trichloropropene. Thereupon the ensuing mixture was maintained for 4 hours at boiling temperature. After cooling down, 100 ml of diethyl-ether were added to the mixture, then the mixture was washed with water and dried on anhydrous $Na_2SO_4$.

After removal of the solvent and the excess of amine, under vacuum in a rotatory evaporator, there remained an oil, N-(1,1-dimethylpropargyl)-N-(3,3-dichloroallyl) amine, which later on becomes a low-melting solid. Elemental analysis gave the following results:

| Theoretical Cl: | 36.92% | found Cl: | 35.98% |
| Theoretical C: | 50.02% | found C: | 48.42% |
| Theoretical H: | 5.77% | found H: | 6.15% |
| Theoretical N: | 7.29% | found N: | 7.18%. |

To 0.04 mols of the amine thus obtained, dissolved in 150 ml of dichloroethane, wherein there had been suspended 0.05 mols of $NaHCO_3$, there were added dropwise and under stirring, at boiling temperature of the mixture, 0.04 mols of dichloroacetylchloride, diluted in 20 ml of the same solvent. Once the addition was completed, the mixture was maintained at the boiling temperature until development of $CO_2$ had ceased. After cooling down, the mixture was first washed with HCl (3% aqueous solution) and then with water.

By removal of the solvent from the solution previously dried on anhydrous $Na_2SO_4$, there was obtained N-(1,1-dimethylpropargyl)-N-(3,3-dichlorallyl)-dichloroacetamide, a low-melting solid. The elementary analysis showed the following composition:

| Theoretical Cl: | 46.79% | found Cl: | 43.59% |
| Theoretical C: | 39.64% | found C: | 40.79% |
| Theoretical H: | 3.66% | found H: | 3.86% |
| Theoretical N: | 4.62% | found N: | 4.47% |

The IR spectrum proved consistent with the assigned formula.

EXAMPLE 2

Preparation of N-ethyl-N-(3,3-dichloroallyl)-dichloroacetamide (our mark: M 8990).

To 1.2 mols of ethylamine, dissolved in an equal volume of benzene, there were added dropwise and under stirring, at room temperature, 0.3 mols of 3,3 1-trichloropropene. Once the addition was completed, the mixture was maintained at the boiling point for 3 hours. After cooling down, the mixture was washed with water and thereupon dried on $Na_2SO_4$.

By removal of the solvent and the excess of ethylendiamine, there remained a liquid, N-ethyl-N-(3,3-dichloroallyl)-amine, which under a pressure of 15 mm distilled at between 61° C. and 63° C.

From this distillate, by the reaction of it with dichloroacetyl chloride, according to the procedures described in the preceding example 1, there was obtained N-ethyl-N-(3,3-dichloroallyl)-dichloroacetamide, a brown oil. The elementary analysis showed the following composition:

| Theoretical Cl: | 53.52% | found Cl: | 50.87% |
| Theoretical C: | 31.73% | found C: | 33.20% |
| Theoretical H: | 3.42% | found H: | 3.89% |
| Theoretical N: | 5.29% | found N: | 5.18% |

The IR spectrum proved consistent with the assigned formula.

EXAMPLE 3

Into a set of pots, having an upper diameter of 10 cm and a height of 10 cm, and containing sandy soil, and in each of which there had been sown a certain infesting weed (see table) and maize there was added as much water as was necessary for a good germination of the seeds. Immediately thereafter a series of these pots was treated with the herbicide N-(2-methyl-6-ethyl-phenyl)-N-(isopropyl-carboxymethyl)-chloroacetamide (mark: HS 26910), in the form of a hydroacetonic dispersion (20% vol/vol), in a dose of 4 kg/ha of active principle, by superficial application to the soil followed by the covering up of it with a 0.5 cm layer of further soil.

A second series of pots was treated under the same conditions, with the herbicide N-(2,6-diethyl-phenyl)-N-(ethyl-carboxymethyl) chloroacetamide (Antor, Hercules) in the same dose.

A third and a fourth set of pots were then treated, under the same conditions, with hydroacetonic dispersions respectively containing herbicide HS 26910 and herbicide Antor, each of which was added with antidotes M 8900 and, separately, to M 8991, in different ratios so as to always obtain a dose of 4 kg/ha of herbicide together with a dose of 0.05 to 0.4 kg/ha of one or of the other antidotes.

For comparative purposes, still another two sets of pots were treated under the same conditions with two hydroacetonic dispersions containing respectively herbicide HS 26910 and Antor, each of which, additioned with antidote N-diallyl-dichloroacetamide (mark: R 25788 Stauffer) in the same proportions used for the two antidotes M 8990 and M 8991.

Still another set of pots in which only maize was sown, was treated with a hydroacetonic dispersion of antidotes M 8990 and M 8991 only, in doses varying from 0.05 to 0.4 kg/ha. This application had no negative effects on the maize plants.

A last set of pots was kept as witness, without any kind of treatment with foreign substances. All the sets of pots were kept under observation in a conditioned environment maintained at a temperature comprised between 15° C. and 24° C., with a relative humidity of 70%, with a light period of 12 hours and with a luminous intensity of 2500 lux.

Every two (2) days, all pots were uniformly sprinkled so as to ensure a degree of humidity sufficient for a satisfactory growth of the plants.

After 14 and 21 days after the treatment, there were carried out determinations of the vegetable state of the plants with evaluations expressed in terms of a scale of values ranging from 0 (equal to a growth equal to that of the witness plants) up to 4 (equal to a complete stop of the growth).

In the following table there have been recorded the results obtained under each of the indicated conditions, and for each plant that has been studied.

From the table the following appears quite clearly, R-25788, without, however being completely eliminated even by the dose of 0.4 kg/ha.

(4) The two antidotes according to the invention develop a protective acitivity on the maize at least double than that of the compounds claimed in DOS No. 2,747,814.

TABLE

Herbicide activity of the esters of N-N-disubstituted glycine on infesting weeds and on maize compared to the activity in the presence of antidotes according to the present invention and according to U.S. Pat. No. 4,021,224 and DOS 2,747,814.

| Applied Substance | Dose kg/ha | Infesting Plants (**) after 21 days from treatment | | | | | | | | MAIZE After 14 days from treatment | MAIZE After 21 days from treatment |
|---|---|---|---|---|---|---|---|---|---|---|---|
| | | E | A | L | SO | SE | V | R | G | | |
| HS 26910 | 4 | 4 | 4 | 4 | 4 | 4 | 4 | 4 | 4 | 3 | 3 |
| HS 26910 + M 8990 | 4 + 0.4 | | | | " | | | | | 0 | 0 |
| HS 26910 + M 8990 | 4 + 0.2 | | | | " | | | | | 0 | 0 |
| HS 26910 + M 8990 | 4 + 0.1 | | | | " | | | | | 0 | 0 |
| HS 26910 − M 8990 | 4 + 0.05 | | | | " | | | | | 0.5 | 0.5 |
| HS 26910 + M 8991 | 4 + 0.4 | | | | " | | | | | 0 | 0 |
| HS 26910 + M 8991 | 4 + 0.2 | | | | " | | | | | 0 | 0 |
| HS 26910 + M 8991 | 4 + 0.1 | | | | " | | | | | 0 | 0 |
| HS 26910 + M 8991 | 4 + 0.05 | | | | " | | | | | 0.5 | 0.5 |
| HS 26910 + M 7601(***) | 4 + 0.4 | 26910 | " | | | | | | 0 | 0 | |
| HS 26910 + M 7601(***) | 4 + 0.2 | | | | " | | | | | 0 | 0 |
| HS 26910 + M 7601(***) | 4 + 0.1 | | | | " | | | | | 1 | 1 |
| HS 26910 + M 7601(***) | 4 + 0.05 | | | | " | | | | | 1.5 | 1.5 |
| HS 26910 + R 25768(*) | 4 + 0.4 | | | | " | | | | | 1 | 1 |
| HS 26910 + R 25768(*) | 4 + 0.2 | | | | " | | | | | 2 | 2 |
| HS 26910 + R 25788(*) 4 + 0.1 | | | | | " | | | | 2.5 | 2.5 | |
| HS 26910 + R 25788(*) | 4 + 0.05 | | | | " | | | | | 2.5 | 2.5 |
| ANTOR | 4 | | | | " | | | | | 3 | 3 |
| ANTOR + M 8990 | 4 + 0.4 | | | | " | | | | | 0 | 0 |
| ANTOR + M 8990 | 4 + 0.2 | | | | " | | | | | 0 | 0 |
| ANTOR + M 8990 | 4 + 0.1 | | | | " | | | | | 0 | 0 |
| ANTOR + M 8990 | 4 + 0.05 | | | | " | | | | | 0 | 0 |
| ANTOR + M 8991 | 4 + 0.4 | | | | " | | | | | 0 | 0 |
| ANTOR + M 8991 | 4 + 0.2 | | | | " | | | | | 0 | 0 |
| ANTOR + M 8991 | 4 + 0.1 | | | | " | | | | | 0 | 0 |
| ANTOR + M 8991 | 4 + 0.05 | | | | " | | | | | 0 | 0 |
| ANTOR + M 7601(***) | 4 + 0.4 | 4 | 4 | 4 | 4 | 4 | 4 | 4 | 4 | 0 | 0 |
| ANTOR + M 760(***) | 4 + 0.2 | | | | " | | | | | 0 | 0 |
| ANTOR + M 7601(***) | 4 + 0.1 | | | | " | | | | | 1 | 1 |
| ANTOR + M 7601(***) | 4 + 0.05 | | | | " | | | | | 1.5 | 2 |
| ANTOR + R 25788(*) | 4 + 0.4 | | | | " | | | | | 1 | 1.5 |
| ANTOR + R 25788(*) | 4 + 0.2 | | | | " | | | | | 1.5 | 2 |
| ANTOR + R 25788(*) | 4 + 0.1 | | | | " | | | | | 2.5 | 2.5 |
| ANTOR + R 25788(*) | 4 + 0.05 | | | | " | | | | | 2.5 | 2.5 |

(*)COMPARATIVE ANTIDOTE (U.S. Pat. No. 4,021,224)
(**)E = echinochloa cruss-galli; A = Avena fatua; L = Loliul italicum; SO = Sorghum spp; SE = Setaria glauca; V = Vigna sinensis; R = Rumex crispus; G = Galensoga parvifera.
(***)= Comparative antidote (DOS 2,747,814)

i.e.:
(1) Both tested herbicides proved phytotoxic for maize showing a toxicity degree of around 3 or 4 at a dose of 4 kg/ha.
(2) The application of either one of the two herbicides, HS 26910 and Antor at the dose of 4 kg/ha in addition with one or the other of the substances, M 8990 or M 8991, in doses from 0.1 to 0.4 kg/ha, eliminates completely the damage caused to the maize by the two herbicides applied singly, without, however, reducing the herbicide activity against the infesting weeds.
(3) The damage inflicted to maize by the application of either one of the two herbicides HS 26910 and Antor, in doses of 4 kg/ha is attenuated proportionally to the addition of growing doses of antidote

What we claim is:
1. Compounds of formula:

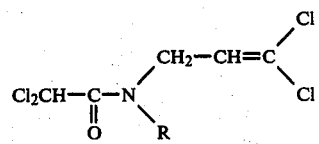

wherein R=ethyl or 1,1-dimethylpropargyl.
2. N-(3,3-dichloroallyl)-N-ethyl-dichloroacetamide of formula:

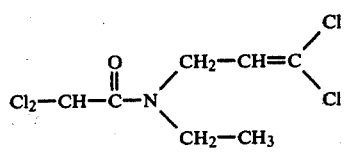
3. N-(1,1-dimethylpropargyl)-N-(3,3-dichlorallyl)-dichloroacetamide of formula:
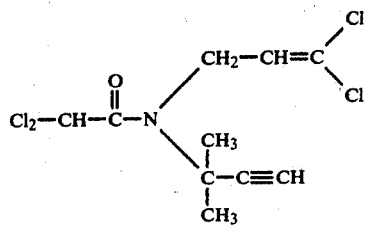
* * * * *